United States Patent [19]
Smith

[11] Patent Number: 6,160,159
[45] Date of Patent: Dec. 12, 2000

[54] PREPARATION OF DIMETHYL TEREPHTHALATE VIA THE AIR OXIDATION OF P-TOLUALDEHYDE

[75] Inventor: Brad Lee Smith, Wilmington, N.C.

[73] Assignee: Arteva North America, S.a.r.l., Zurich, Switzerland

[21] Appl. No.: 09/365,325

[22] Filed: Jul. 30, 1999

Related U.S. Application Data

[63] Continuation-in-part of application No. 09/069,598, Apr. 29, 1998, abandoned.

[51] Int. Cl.⁷ ............................. C07C 67/00; C07C 51/16
[52] U.S. Cl. ............................. 560/77; 562/407; 562/409
[58] Field of Search ............................... 560/77; 562/407; 462/409

[56] References Cited

U.S. PATENT DOCUMENTS

| | | |
|---|---|---|
| 4,353,810 | 10/1982 | Wendle, Jr. . |
| 4,820,862 | 4/1989 | Hoffmann et al. ..................... 560/77 |
| 5,679,847 | 10/1997 | Ohkoshi et al. . |

FOREIGN PATENT DOCUMENTS

| | | |
|---|---|---|
| 2 425 763 | 5/1974 | Germany . |
| 27 33 548 | 7/1977 | Germany . |
| 51-86433 | 7/1976 | Japan . |
| 51-86436 | 7/1976 | Japan . |
| 51-86437 | 7/1976 | Japan . |
| 51-91223 | 8/1976 | Japan . |
| 54-063037 | 5/1979 | Japan . |

*Primary Examiner*—Johann Richter
*Assistant Examiner*—J. Parsa
*Attorney, Agent, or Firm*—Gregory N. Clements

[57] ABSTRACT

The invention is directed to a process for the production of terephthalic acid and esters thereof from p-tolualdehyde or mixtures of p-tolualdehyde and p-xylene. The process of the invention can be carried out at lower temperatures and faster throughput than conventional processes using p-xylene. The use of p-tolualdehyde facilitates safety considerations by eliminating the induction period and high oxiding fluid concentrations encountered in typical oxidation reactions which use only p-xylene as the terephthalic acid or ester precursor.

46 Claims, 5 Drawing Sheets

PREPARATION OF DIMETHYL TEREPHTHALATE VIA THE AIR OXIDATION OF P-TOLUALDEHYDE

This application is a continuation-in-part of application No. 09/069,598, filed Apr. 29, 1998, now abandoned.

FIELD OF THE INVENTION

The invention is directed to the preparation of dimethyl terephthalate (DMT), and in particular to the preparation of same via the air oxidation of p-tolualdehyde in the presence or absence of other DMT precursor or intermediate compounds.

BACKGROUND OF THE INVENTION

The preparation of DMT is a well known process exemplified by the Witten process which utilizes p-xylene as a starting material. In the Witten process, the preparation of DMT can proceed via two pathways generally represented below as Routes 1 and 2.

In Route 1, p-xylene is oxidized [Ox], using methods known to one of ordinary skill in the art, to PTA which in turn is oxidized to TA. TA is subsequently esterified using methanol, with the removal of by-product water, to form DMT. In Route 2, after p-xylene is oxidized to PTA, the PTA is esterified with methanol to form MPT. The MPT is then further oxidized to MMT which in turn is esterified with methanol to form DMT.

In accordance with both of Routes 1 and 2 an intermediate oxidation takes place whereby p-xylene is first oxidized to p-tolualdehyde, which, in turn, is oxidized to p-toluic acid. Thus, the first step of each of Routes 1 and 2 as shown above may also be represented as follows:

In the foregoing process as generally described, an oxidation catalyst is used in the various oxidation steps. While the art frequently mentions the use of "heavy metals" or "heavy metal salts" as oxidation catalysts, in current commercial practice the catalyst is usually cobalt acetate as the sole or major oxidation catalyst component. When a co-catalyst is used, it is usually manganese acetate. These metal salts are water soluble and the total concentration of metal catalyst(s) is generally in the range 0.001–0.1 wt % of the total oxidation reaction mixture. The oxidation catalysts are employed in all oxidation steps in both Routes 1 and 2 described above.

It is recognized that Routes 1 and 2 contain multiple oxidation and esterification steps. This results in considerable capital outlay for multiple reactor sections and in large operating cost outlays for the multiple processing steps. Further, because the rate of oxidation of p-xylene is relatively slow, large steady-state concentrations must be maintained in commercial operations in order to make the process commercially viable. Overall, it would be advantageous if capital and operating costs could be lowered by improvements in the process.

U.S. Pat. No. 4,353,810 (the '810 patent) describes a process for the production of DMT. As described in the '810 patent, the DMT process charges p-xylene, methyl p-toluate (MPT), air (the oxidizing agent) and the oxidation catalyst (s) to a first oxidation stage at a selected oxidation temperature for a selected oxidation time to produce a first oxidation mixture or oxidate. The oxidate is withdrawn from the first stage and passed to a first esterification stage, with or without removal and recycle of unreacted p-xylene. Methanol is admixed with the oxidate and esterification is carried out at a selected temperature for a selected time. Subsequent to esterification, the reaction mixture is distilled to yield MPT (and p-xylene if not previously separated) overhead and a first bottoms fraction. The MPT (and any p-xylene) is returned to the first oxidation stage and the first bottoms fraction is further distilled to yield at least a DMT fraction and a second bottoms fraction. The DMT may be further purified as required and the second bottom fraction may be "discarded" generally by combustion) or recycled, with or without further processing steps. Due to cost and environmental consideration, it is preferred that the second bottoms fraction be recycled or at least the catalyst(s) recovered before the fraction is discarded.

U.S. Pat. No. 5,679,847 to Ohkoshi et al, assigned to Mitsubushi Gas Chemical Co., discloses a process for producing terephthalic acid by oxidizing a liquid-phase starting raw material containing p-xylene having 3 to 35 weight percent p-tolualdehyde based on the same at a temperature in the range of 120° to 240° C. by means of an oxygen-containing gas using a lower aliphatic monocarboxylic acid such as acetic acid, propionic acid or butyric acid as a solvent in the presence of a bromine compound, a manganese compound catalyst and a cobalt compound catalyst. Caution must be exercised during the process to avoid oxidation loss of the solvent monocarboxylic acid.

Japan Open Patent No. 9122311976 (filed Feb. 10, 1976) to Mitsubishi Gas Chemical (MGC1) describes a process for producing terephthalic acid by the liquid phase oxidation of p-tolualdehyde with an oxygen-containing fluid in the presence of a catalyst combination consisting of a manganese compound, a cobalt compound, a bromine compound and a lanthanide(s) metal compound. Additional MGC patents describing the use of p-tolualdehyde include Japan Open Patent Nos. 86433/1976 (hereafter MGC2, "Manufacturing Method of Aromatic Carboxylic Acids and/or Their Methyl Esters"), 86436/1976 (hereafter MGC3, "Manufacturing Method of Toluic Acid from Tolualdehyde"), and 86437/1976 (hereafter MGC4, "Preventing Method of Formation of Black Colored Phthalic Acid"). While the four MGC disclosures discuss the use of p-tolualdehyde in the production of terephthalic acid, they also reveal a serious defect in that the resulting product is frequently black or black-flecked due to the presence of manganese containing substances. Consequently, while the art for the production of TA or DMT is well advanced, further improvements are still desirable. In particular, improvements in product color, reduction of steady-state concentrations, reduced reaction temperature and time, improved reaction rate and/or selectivity, and improved safety are particularly desired.

It is an object of the present invention to describe a process for the production of DMT from p-tolualdehyde, or a reaction mixture containing p-tolualdehyde and additional DMT precursor substances.

It is an object of the present invention to describe a process for the production of DMT from p-tolualdehyde or a p-tolualdehyde-containing reactive mixture whereby the steady-state concentration of feed material may be reduced without loss of overall product output.

It is a further object of the invention to describe a process for the production of DMT having improved safety considerations due to reduced oxidizer oxygen concentrations during startup.

It is an additional object of the invention to describe a process for the production of DMT in which the use of one or more catalysts is reduced or eliminated.

SUMMARY OF THE INVENTION

The invention is directed to a process for using p-tolualdehyde for the production of dimethyl terephthalate or terephthalic acid.

More particularly, the present invention provides a process for producing terephthalic acid and/or one or more esters thereof which comprises oxidizing p-tolualdehyde with an oxygen-containing fluid and, when one or more esters are to be produced, reacting the resulting oxidation product with an alcohol.

According to an embodiment of the invention, the process comprises producing terephthalic acid and one or more esters thereof by oxidizing a feedstock containing p-tolualdehyde with an oxygen-containing fluid to terephthalic acid and one or more esters thereof, wherein the formation of said one or more esters is effected by the additional step of adding an alcohol, preferably methanol, at one or more intervals during the oxidation process or at the end of the oxidation process or both. When the alcohol is added at one or more intervals during the oxidation process, this is done between stages of the oxidation process at which intermediates having successively higher degrees of oxidation are formed, preferably between the oxidation of p-tolualdehyde to p-toluic acid and the oxidation of a p-toluate, especially methyl p-toluate, to form the corresponding monoester of terephthalic acid, especially monomethyl terephthalate, whereby said p-toluate is produced from said p-toluic acid and said alcohol. When the alcohol is added at the end of the oxidation process, this may be done after the oxidative formation of terephthalic acid and/or after the oxidative formation of said monoester of terephthalic acid.

According to a particular embodiment of the invention, terephthalic acid or an ester thereof is produced by a process comprising the steps of (a) oxidizing at a first selected temperature a feedstock selected from the group consisting of p-tolualdehyde- and p-tolualdehyde/p-xylene-containing feedstocks with an oxygen-containing fluid to produce p-toluic acid; and (b) carrying out a step selected from the group consisting of (1) esterifying the product of step (a) with methanol to form methyl p-toluate and oxidizing at a second selected temperature the methyl p-toluate with an oxygen-containing fluid to form monomethyl terephthalate., (2) oxidizing the product of step (a) with an oxygen-containing fluid to form terephthalic acid.

A further embodiment of the present invention comprises the additional step of (c) esterifying the product of step (b) with methanol to form a reaction product containing dimethyl terephthalate.

A still further embodiment of the invention comprises the additional step of (d) separating the dimethyl terephthalate from the product of step (c).

Preferably, in step (b) both of steps (b)(1) and (b)(2) take place during the same process.

The present invention is distinguished from the known Witten process described above in that, in addition to or in place of p-xylene, p-tolualdehyde is added as a starting raw material to the oxidation reactor for oxidation to p-toluic acid.

Preferably, in a process according to this invention methyl p-toluate is oxidized to monomethyl terephthalate in a reaction vessel to which added p-tolualdehyde is fed. More preferably, added p-tolualdehyde is fed to said reaction vessel during oxidation of the methyl p-toluate. Most preferably, the methyl p-toluate is oxidized in the same reaction mixture in which the p-tolualdehyde is oxidized. In a continuous process this can be done by carrying out the process in the manner described in the aforementioned U.S. Pat. No. 4,353,810 but adding p-tolualdehyde in place of or in addition to p-xylene as a starting raw material. The disclosure of U.S. Pat. No. 4,353,810, particularly from column 1, line 17 to column 2, line 6, is incorporated herein by reference. In a batch process the methyl p-toluate can be added as part of an initial charge to an oxidation reactor to which p-tolualdehyde-containing starting raw material is fed. The reaction product from that reactor, which is subsequently transferred an esterifier, will contain monomethyl terephthalate, which becomes esterified to dimethyl terephthalate, and p-toluic acid, which becomes esterified to methyl p-toluate. Upon completion of the esterification, the methyl p-toluate can be separated from the dimethyl terephthalate, e.g. by distillation, and used with p-tolualdehyde as the starting material in a subsequent batch-type oxidation.

As indicated above, the oxidation of p-tolualdehyde or p-tolualdehyde/p-xylene results in the production of p-toluic acid, which, in turn, can be esterified to methyl p-toluate in a process according to the present invention. As also described above, and as an embodiment of the present invention, p-toluic acid can be oxidized to terephthalic acid, which, in turn, can be esterified to dimethy terephthalate. When p-toluic acid is oxidized to terephthalic acid in accordance with the present invention, this is preferably done in a reaction vessel to which added p-tolualdehyde is fed. More preferably, added p-tolualdehyde is fed to said reaction vessel during the oxidation of the p-toluic acid. Most preferably, the p-toluic acid is oxidized by carrying out the oxidation in the same reaction mixture in which the added p-tolualdehyde is being oxidized to p-toluic acid.

Preferably, the esterification of p-toluic acid to methyl p-toluate and the esterification of monomethyl terephthalate to dimethyl terephthalate are carried out together in the same esterification reactor, as taught by U.S. Pat. No. 4,353,810.

A process according to this invention may be carried out as follows:

1. p-Tolualdehyde and preferably p-xylene as starting raw material(s) and recycled methyl p-toluate are continuously introduced along with an oxygen-containing fluid into an oxidation reactor (oxidizer), which is maintained under conditions effective for the production of an oxidate reaction product comprising p-toluic acid and monomethyl terephthalate and, preferably, terephthalic acid.

2. Oxidate reaction product is continuously removed from the oxidizer and, after optional stripping to remove unreacted p-xylene (which may be recycled to the oxidizer), fed to an esterification reactor (esterifier) to which methanol is also continuously fed and which is maintained under conditions effective for the esterification of p-toluic acid to methyl p-toluate and the esterification of monomethyl terephthalate and, preferably, terephthalic acid to dimethyl terephthalate.

3. Esterified reaction product is continuously removed from the esterifier and fed to a still in which methyl p-toluate is separated from dimethyl terephthalate, with the former being recycled to the oxidizer and the latter preferably being subjected to further purification.

Comparing the steady-state concentrations of p-tolualdehyde in the process of the invention and p-xylene in known processes, the steady state concentration of p-tolualdehyde in the process of the invention is reduced relative to the steady-state concentration of p-xylene in known processes, thereby providing for a greater effective reactor volume which results in increased material throughput and product output. The process further provides for greater plant safety because it lacks the prolonged oxidation induction period at startup, thereby decreasing the overall oxygen requirements, lowering operating temperature, and decreasing by-products.

DETAILED DESCRIPTION OF THE INVENTION

As used herein, the term "feedstock" means any hydrocarbon or hydrocarbon mixture suitable for use in the production of dime thyl terephthalate, and shall include p-tolualdehyde and p-tolualdehyde/p-xylene mixtures either alone or admixed with other hydrocarbons such as toluic acid, monomethylterephthalate, terephthalic acid, ethylbenzene, methyl p-toluate, and similar hydrocarbons and oxidation or degradation products thereof.

As used herein, the term "catalyst" means any metal or metal salt capable of carrying out the indicated catalytic reaction. Examples of such catalysts includes the acetate, chloride, bromide, oxalate, stearate, sulfate, and similar salts of cobalt, manganese, nickel and other metal catalysts known to those skilled in the art.

Dimethyl terephthalate is an aromatic dicarboxylic acid diester widely used in the production of polyester materials and for other purposes. The present invention describes an improved process for the production of DMT from p-tolualdehyde or a p-tolualdehyde containing feedstock. p-Tolualdehyde oxidizes in the presence of an oxygen containing fluid to form PTA at a rate about twenty-two times faster than the rate at which p-xylene can be oxidized to the same product. Furthermore, when p-tolualdehyde is used in place of some or all of the p-xylene, the steady-state concentration of feed material in the oxidizer can be reduced. This reduction in steady state concentration results in greater available reactor volume.

Preferably, the p-tolualdehyde is added to the reactor in which it, and preferably the p-toluic acid or methyl p-toluate, more preferably both, is are oxidized as a feed stock containing at least 0.5%, more preferably at least 1.0%, most preferably 5 to 95%, especially to 90% and more especially 65 to 90%, based on the total weight of p-tolualdehyde and p-xylene being added. This includes any p-xylene which might be recycled to the reactor, for example from an optional p-xylene stripping step.

p-Tolualdehyde for use in the present invention can be obtained by methods known in the art, for instance by synthesis from toluene and carbon monoxide in the presence of $HF.BF_3$ catalyst according to the Gattermann-Koch reaction, followed by distillation to remove o-tolualdehyde or by the method disclosed in U.S. Pat. No. 5,910,613, the disclosure of which is incorporated herein by reference.

The rate of production of DMT is controlled by the rates at which MPT and PTA oxidize. When p-tolualdehyde is added to p-xylene, or when p-tolualdehyde is used by itself, the rates of MPT and PTA oxidation increase as is shown below in Table 1 of Example 2. In Example 2, it was determined that when p-tolualdehyde and p-xylene are fed to the oxidation reactor in identical molar rates, nearly twice as much intermediate MPT and PTA are oxidized to MMT and TA in the case of p-tolualdehyde as compared to the p-xylene case.

It has also been found that the use of p-tolualdehyde aids in the oxidation of MPT and PTA even when no cobalt and/or manganese catalysts are used. As exemplified by the prior art, catalysts such as cobalt and manganese catalyst are required for the oxidation of p-xylene. However, as shown below in Example 4, when p-tolualdehyde is used in place of p-xylene, the oxidation of PTA and MPT in the absence of a catalyst proceeds at rates approximating that of p-xylene in the presence of 200 ppm or higher cobalt catalyst. The use of a p-tolualdehyde process containing no cobalt or reduced levels of cobalt will have several advantages over the current art. First, cobalt salts are known to foul esterification trays and distillation reboilers. Eliminating the use of cobalt salts would eliminate or minimize these problems, reduce equipment down-time, increase output, and generally result cost savings. Second, in current processes cobalt must be recovered from the purge streams due to the cost of the catalyst. Eliminating or minimizing the use of cobalt salts would again result in cost savings.

Figure 3:
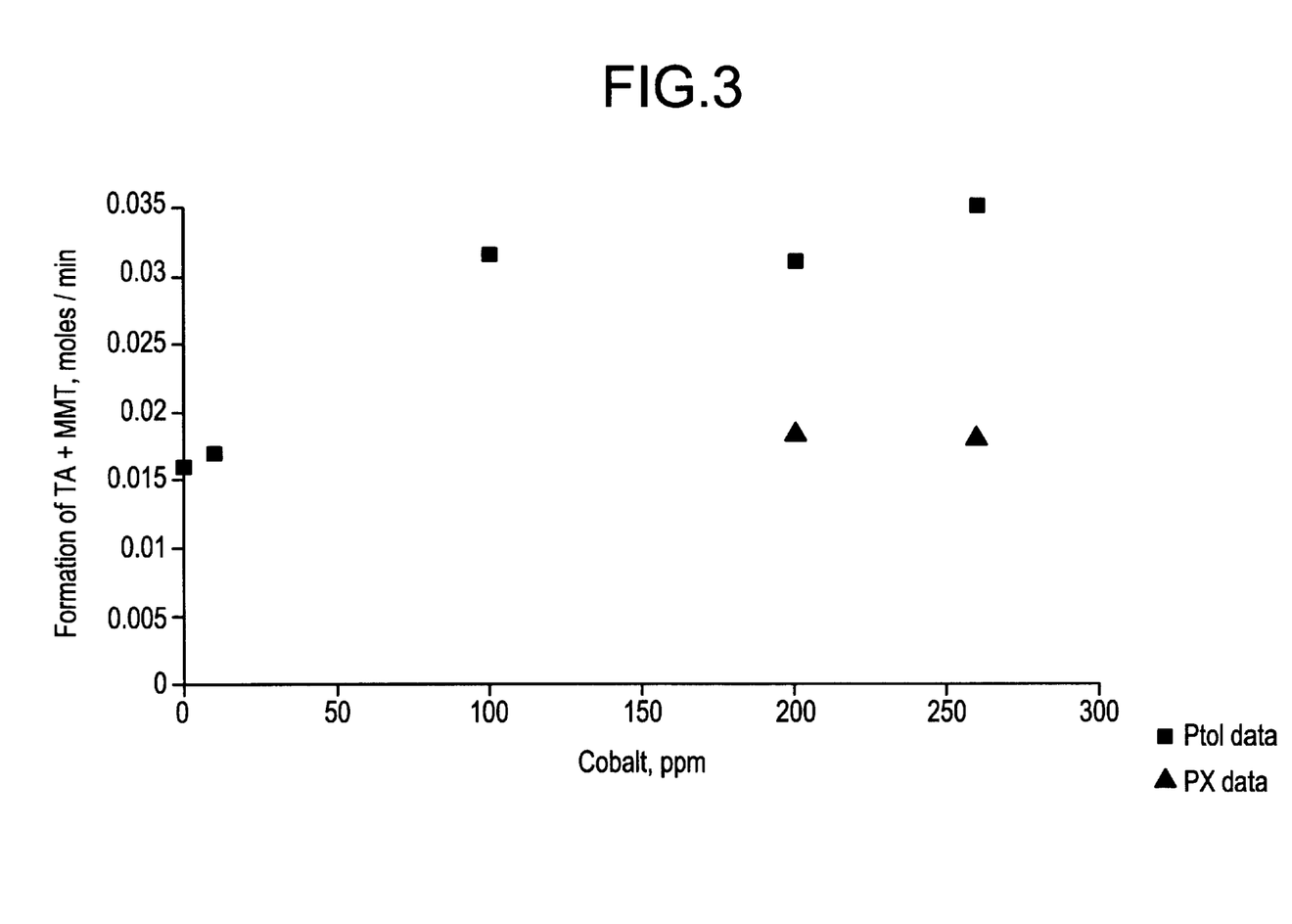
FIG. 3 illustrates the effect of the cobalt catalyst concentration on the rate of formation of TA and MMT with p-tolualdehyde (no p-xylene) and p-xylene (no p-tolualdehyde) feedstocks.

Oxidation temperature can be reduced when p-tolualdehyde is used in whole or in part in the place of p-xylene as is illustrated by FIG. 3. Lower oxidation temperatures generally result in decreased burning losses and lower condenser energy requirements. According to the present invention, the oxidation temperatures of the various oxidation steps are within the range of about 100° to about 200° C., preferably about 130° to about 180° C., and most preferably from about 150° to about 170° C.

An added advantage to using p-tolualdehyde or mixtures of p-xylene and p-tolualdehyde is that the oxidation process does not have an induction period. When p-xylene alone is oxidized by an oxygen containing fluid, there is always an induction period. In batch processes, this induction period can be from 5 to 20 minutes, or more. Similar induction periods are also observed during startup of commercial continuous processes. During these induction periods, the oxygen concentration in the system can build up to higher levels than would normally be encountered in continuous operation. This buildup leads to safety concerns due to the higher than normal concentration of oxygen in the reactor.

The DMT processes of the invention which utilize p-tolualdehyde or p-tolualdehyde/p-xylene mixtures result in a post-oxidation composition which contains very small amounts of p-tolualdehyde, generally less than 1%. Under identical conditions, a p-xylene oxidation yields a post-oxidation composition containing more than 1% p-xylene, e.g. about 7% or even higher amounts, such as 10% shown in Example 6 below. Consequently, utilizing either p-tolualdehyde or a p-tolualdehyde/p-xylene mixture can reduce or eliminate p-xylene buildup and allow for additional available reactor volume corresponding to the reduction in the total amount of p-tolualdehyde and p-xylene in the post-oxidation composition, e.g. up to about 6% or even higher as shown in Example 6.

The oxidations according to the present invention do not require the use of a bromine compound and such compounds are preferably excluded.

The oxidations according to the present invention do not require the presence of an aliphatic monocarboxylic acid as a solvent and such compounds are preferably excluded. As a consequence of this the oxidations may be carried out in a reaction vessel made from stainless steel rather than from a more costly metal.

The following examples are given to illustrate the invention and are not to be taken as limiting the invention. DMT can be produced from p-tolualdehyde or p-tolualdehyde/p-xylene feedstocks in either batch or continuous processes, and the use of batch processes in the examples which follow are not to be taken as a limitation on the invention. Any oxygen-containing fluid may be used in practicing the invention. Air is the preferred fluid.

EXAMPLE 1
General Reaction Conditions and Procedures

Figure 1:
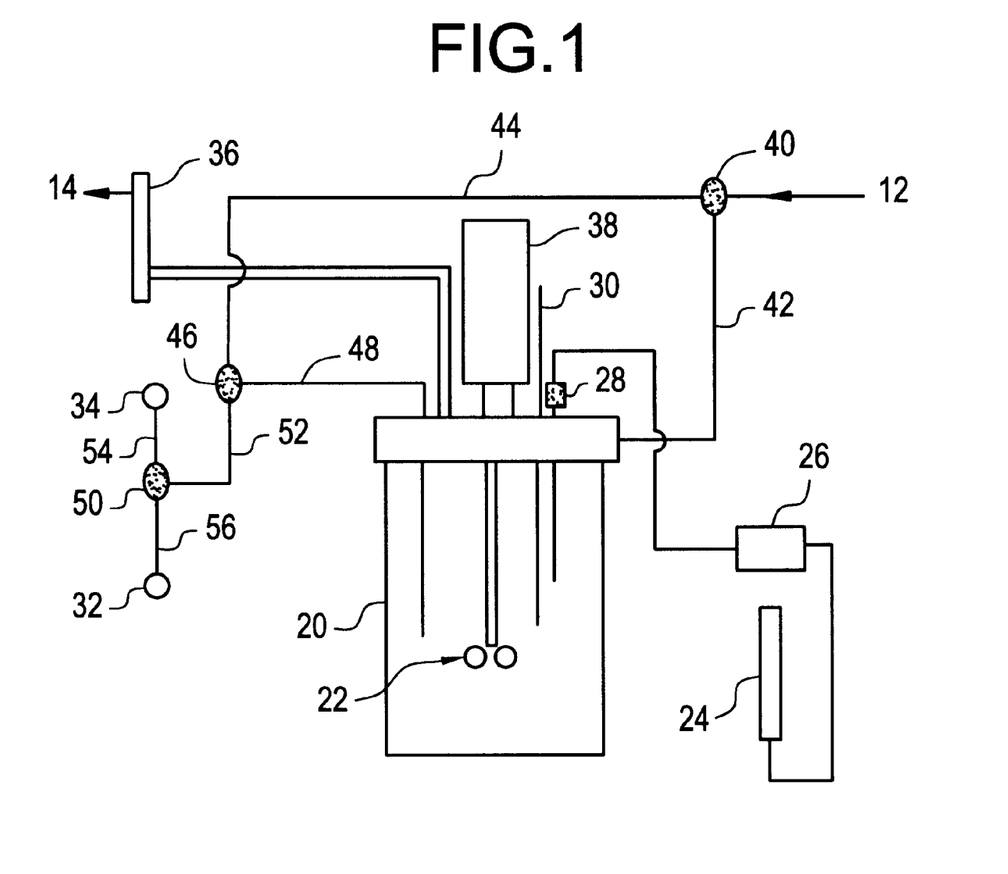
FIG. 1 illustrates the reactor set-up used in the Examples.
Figure 2:
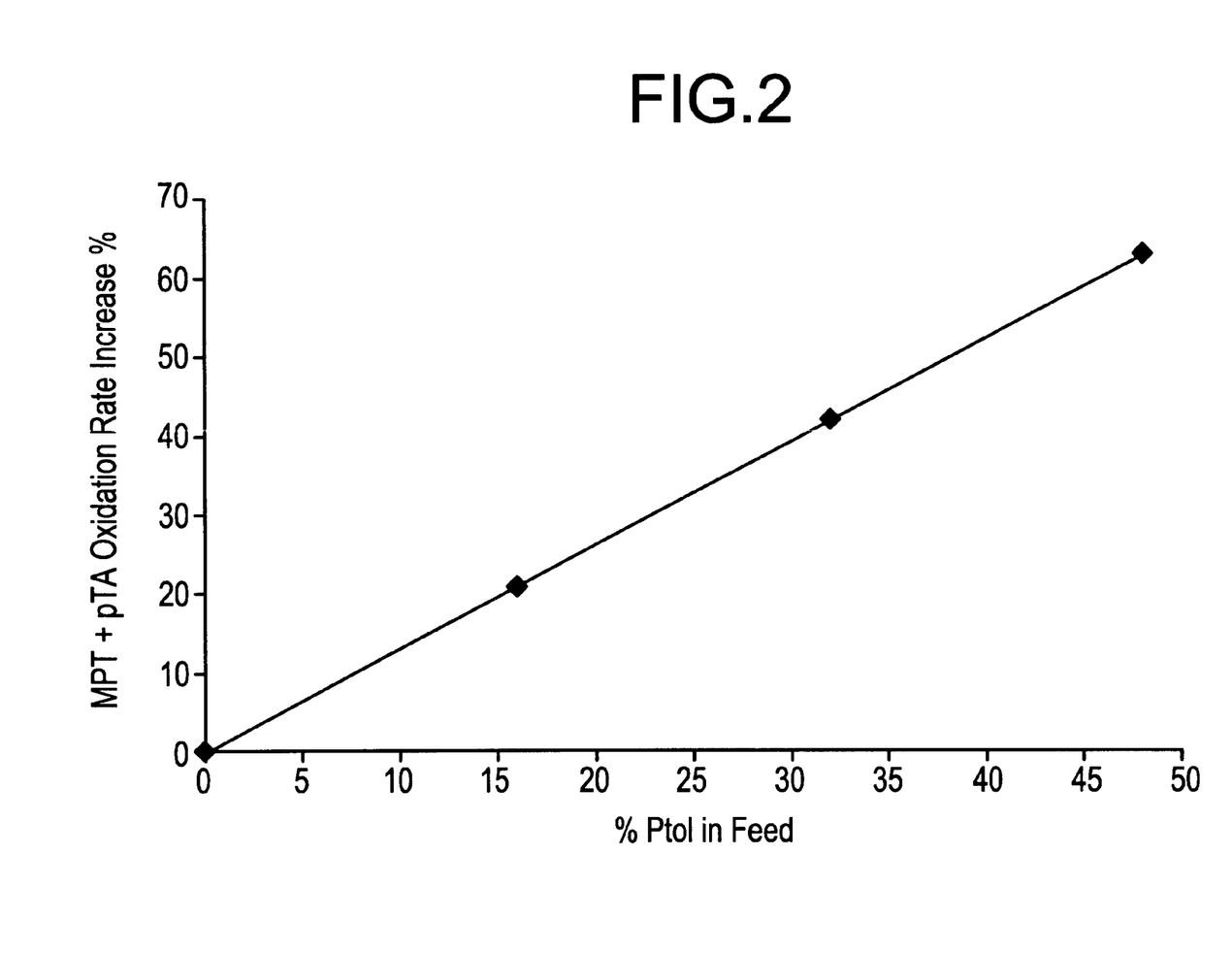
FIG. 2 illustrates the rate of oxidation of MPT and PTA with different percentages of p-xylene in the feedstock.

A one gallon autoclave is charged with 1200g MPT (8.0 mol), 24 g p-toluic acid (0.18 mol), 1.035 g cobalt acetate tetrahydrate and 0.550 g manganese acetate. After charging, the autoclave is closed, purged with nitrogen and heated to a selected reaction temperature of about 165° C. After reaching temperature, the autoclave is pressurized to 100 psig with air. Subsequently, using a syringe pump or similar apparatus suitable for delivering liquids to the autoclave, p-xylene, p-tolualdehyde or a p-tolualdehyde/p-xylene mixture is charged to the autoclave at a rate of about 3 ml/min. Using a back-pressure regulator, air is continuously added to the autoclave such that the pressure is maintained at about 75–125 psig, and preferably at 100 psig. The air 12 is fed at a rate such that the off-gas oxygen concentration maintained at about 10%. Samples of the reaction products may be periodically taken from the reactor by means of a sampling valve thereon. Off-gases 14 are analyzed for CO, $CO_2$ and $O_2$. FIG. 1 illustrates the autoclave and peripheral equipment used in all the Examples. Illustrated are autoclave 20, stirrer 22, burette 24 containing p-xylene, p-tolualdehyde or p-tolualdehyde/p-xylene mixture, pump 26, check valve 28 to prevent back flow from the autoclave, thermocouple thermowell 30, sampling tube 32, purge tube 34, off-gas condenser 36 and control panel 38. With respect to the various lines, their purpose is fully explained by their connections to the equipment described above. Thus, as will be apparent to one skilled in the art, with valve 40 open in the appropriate direction, air or nitrogen will flow via line 42 to autoclave 20 for oxidizing or for purging of the autoclave, respectively. With valve 40 repositioned in the appropriate direction, air will flow via line 44 to valve 46, which can direct it through line 48 for purging of line 48. With valves 46 and 50 each open in the appropriate direction and valve 40 directing air via line 42 to autoclave 20, line 52 can be purged via valve 50 and line 54 to purge tube 34, and with valves 40 and 46 open in the same direction and valve 50 repositioned in the appropriate direction, samples of the reaction product can be transported from autoclave 20 to sampling tube 32 via lines 48, 52 and 56.

EXAMPLE 2
Oxidation Acceleration by p-Tolualdehyde

The purpose of this Example is to demonstrate that replacing p-xylene by p-tolualdehyde accelerates the oxidation of MPT and PTA. The autoclave was set up as in Example 1 and p-tolualdehyde was fed at a rate of 3 ml/min (0.025 mol/min) for eighty (80) minutes. After 80 minutes run time, the air in the autoclave was replaced with nitrogen. The oxidate was then cooled, removed from the autoclave and analyzed by gas chromatography (GC). After completion of the p-tolualdehyde run, the autoclave was again set up as in example 1 and p-xylene was fed at a rate of 3.08 ml/min (0.025 mol/min) for eighty-eight (88) minutes instead of 80 minutes. The additional time was required because there was an eight minute induction period for the p-xylene oxidation. In contrast, there was no induction period for the p-tolualdehyde oxidation. The results of the p-tolualdehyde and p-xylene runs are shown in Table 1.

TABLE 1

| | Oxidation Products MOLES | |
|---|---|---|
| | PTAL RUN | P-XYLENE RUN |
| P-Xylene | 0 | 1.04 |
| PTAL | 0.094 | 0.07 |
| MPT | 3.58 | 5.93 |
| PTA | 1.51 | 1.25 |
| MMT | 3.14 | 1.85 |
| TA | 0.50 | 0.18 |
| Other intermediates | 0.12 | 0.24 |
| Residue compounds | 0.04 | 0.03 |
| CO | 0.38 | 0.17 |
| $CO_2$ | 1.02 | 0.42 |
| Water in Condenser | 3.64 | 3.41 |
| Acid Number (mg KOH/g Sample) | 222 | 123 |
| Total DMT Precursors (DMT after esterification) | 3.64 | 2.03 |

The data of Table 1 indicates that when p-tolualdehyde and p-xylene are fed to the reactor at identical molar rates, the use of p-tolualdehyde results in nearly twice as much MPT and PTA being oxidized to MMT and TA (both zero at the start of the runs) as is the case in the p-xylene run.

The reaction products obtained as described in this example can be subjected to an esterification reaction in known manner to convert the MMT and TA to DMT.

EXAMPLE 3
Rate Enhancement Using p-Tolualdehyde

The purpose of this Example is to illustrate the degree to which the oxidation rate of MPT and PTA is enhanced as p-tolualdehyde is substituted for p-xylene. Several autoclave runs were performed as described in Example 1, except that mixtures of p-tolualdehyde and p-xylene were fed to the reactor at a rate such that the total moles/minute of feed was equal to 0.025 moles/min. The results are illustrated in FIG.

9

EXAMPLE 4
MPT/PTA Oxidation in the Absence of Catalysts

The purpose of this Example is to demonstrate that even in the absence of a catalyst, p-tolualdehyde promotes oxidation of MPT and PTA. Several runs were performed as described in Example 1, except that the amount of cobalt was varied in each run. In each run para-tolualdehyde (only) or p-xylene (only) was fed at the rate of 0.021 moles/min. The results are illustrated in FIG. 3 and indicate that even when p-tolualdehyde is used in the absence of the cobalt catalyst, the oxidation of PTA and MPT proceeds at rates close to those obtained when p-xylene is used with 200 ppm, or higher, cobalt.

EXAMPLE 5
Temperature Effect Using p-Tolualdehyde

Figure 4:
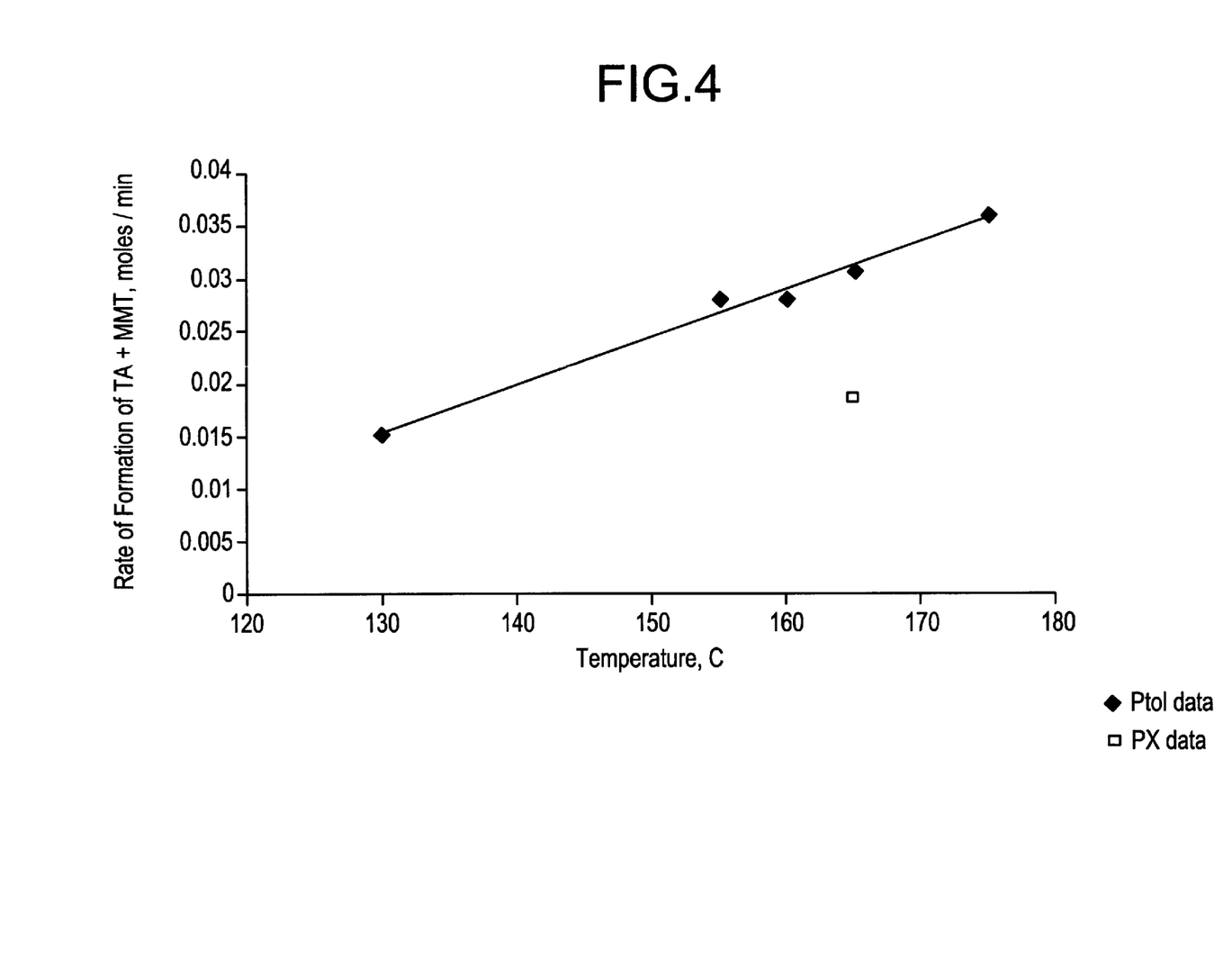
FIG. 4 illustrates the effect of temperature on the rate of formation of MMT and TA with p-tolualdehyde (no p-xylene) and p-xylene (no p-tolualdehyde) feedstocks.

The purpose of this Example is to demonstrate that the use of p-tolualdehyde enables the oxidation of MPT and PTA to proceed at lower temperatures than is the case when p-xylene is used as the feedstock. Several autoclave runs were performed as in Example 1, except that the oxidation temperature was varied. In all runs, the p-tolualdehyde or p-xylene feed rate was 0.021 moles/min. The results are summarized in FIG. 4 and indicate that when p-tolualdehyde is present, the temperature for the oxidation of MPT and PTA to MMT and TA, at a given rate, is lower than is the case when p-xylene is present instead of p-tolualdehyde. For a "MMT plus TA" rate of formation of about 0.19 moles/min, the temperature is about 138° C. for p-tolualdehyde versus about 165° C. for p-xylene.

EXAMPLE 6
Oxidizer Capacity Increase Using p-Tolualdehyde

The purpose of this Example is to demonstrate that oxidizer capacity increases when p-tolualdehyde is used in place of p-xylene. Two autoclave runs were set up as in Example 1. In Run 6A, p-tolualdehyde (only) was fed to the reactor at a rate of 0.025 moles/min. In Run 6B, p-xylene (only) was fed to the reactor at 0.025 moles/min. Samples were periodically taken during both runs and analyzed by GC for p-xylene and p-tolualdehyde. The results are summarized in FIG. 5. In Run 6B, the concentration of p-xylene continuously increases over time and at the end of the run the p-xylene concentration is about 10%. In Run 6A, the p-tolualdehyde concentration remains low throughout the run, the final concentration being less than 1%.

Figure 5:
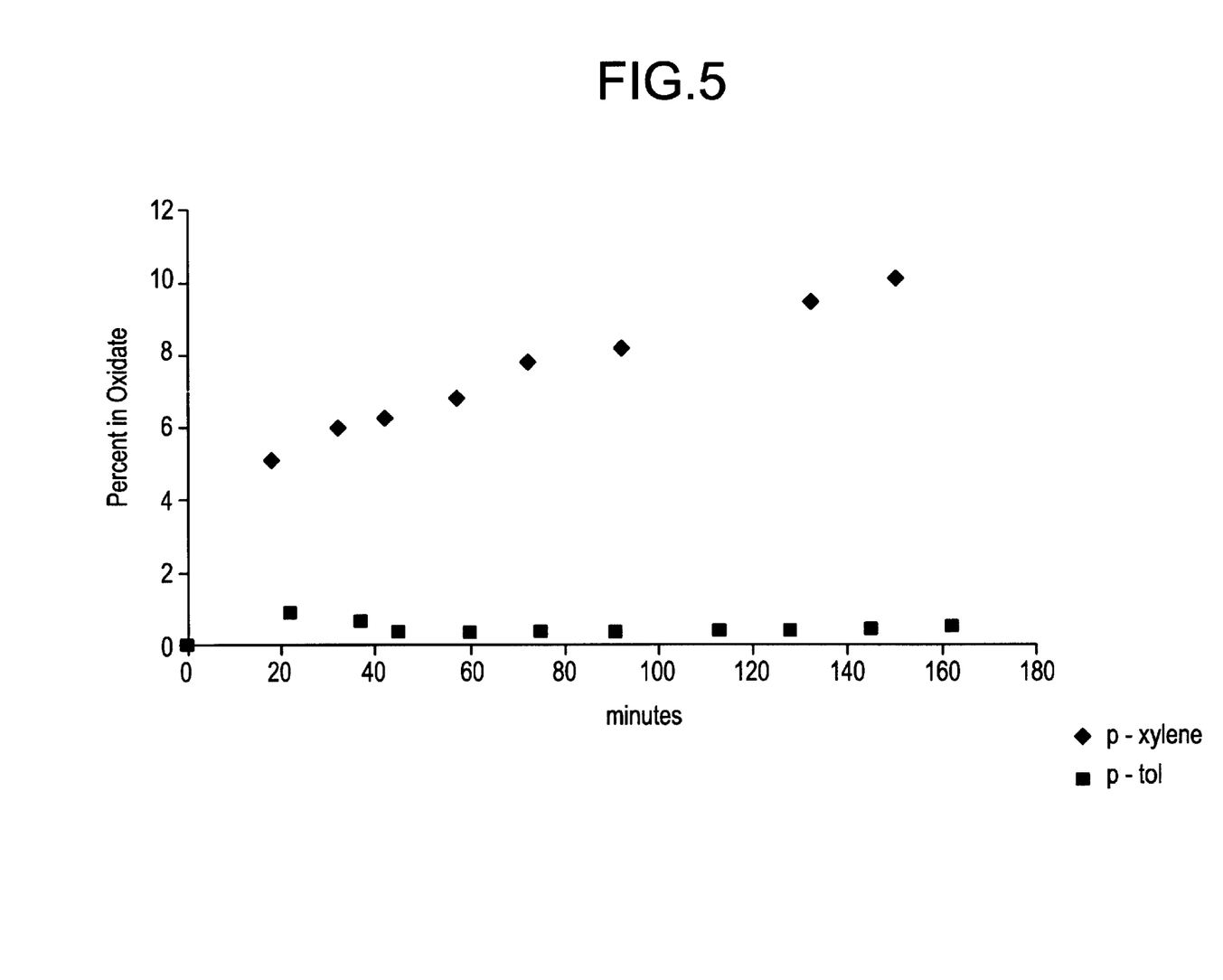
FIG. 5 illustrates the concentration of p-tolualdehyde and p-xylene at various times during the autoclave oxidation runs of the Examples.

The fact that the p-tolualdehyde remains low throughout Run 6A is due to the fact that p-tolualdehyde is more rapidly oxidized than p-xylene. This translates into higher reactant throughput and resulting higher production rates of MMT and TA without the necessity of increasing reactor size or adding additional reactors to the production facility.

The entire disclosure of parent application No. 09/069,598, filed Apr. 29, 1998, is incorporated herein by reference.

After reading the foregoing disclosure, various advantages, features and other specific embodiments of the invention will become readily apparent to one skilled in the art. Such embodiments are within the broad scope of the disclosure and the claims appended hereto. further, while specific examples have been given herein to exemplify the invention, modification and variation of these examples can be carried out without departing from the spirit and the scope of the invention as described.

I claim:

1. A process for the production of dimethyl terephthalate comprising the steps of:
    (a) oxidizing at a first selected temperature a feedstock selected from the group consisting of p-tolualdehyde and p-tolualdehyde/p-xylene containing feedstocks with an oxygen containing fluid to produce p-toluic acid;
    (b) carrying out a step selected from the group consisting of:
        (1) esterifying the product of step (a) with methanol to form methyl p-toluate and oxidizing at a second selected temperature the methyl p-toluate with an oxygen containing fluid to form monomethyl terephthalate, and
        (2) oxidizing the product of step (a) with an oxygen containing fluid to form terephthalic acid;
    (c) esterifying the product of step (b) with methanol to form a product containing dimethyl terephthalate; and
    (d) separating the dimethyl terephthalate from the product of step (c),
wherein the oxidations are carried out in the absence of any bromine compound.

2. The process according to claim 1, wherein the oxidations are carried out in the presence of one or a plurality of oxidation catalysts.

3. The process according to claim 2, wherein the oxidations are carried out in the presence of a cobalt containing catalyst.

4. The process according to claim 2, wherein the oxidations are carried out in the presence of a cobalt containing and a manganese containing catalyst.

5. The process according to claim 1, wherein the selected temperature is from about 100° to about 200° C.

6. The process according to claim 1, wherein the selected temperature is from about 130° to about 180° C.

7. The process according to claim 1, wherein the selected temperature is from about 150° to about 170° C.

8. A process for the production of terephthalic acid and esters thereof, said process comprising at least the step of oxidizing a feed stock containing 5–90% p-tolualdehyde with an oxygen-containing fluid to terephthalic acid and esters thereof, wherein the formation of said esters is by the additional step of adding an alcohol at selected intervals during the oxidation process or at the end of the oxidation process and wherein the oxidizing step is carried out in the absence of any bromine compound.

9. The process according to claim 8 wherein said oxidation is carried out in the presence of one or a plurality of oxidation catalysts.

10. The process according to claim 9, wherein the oxidation is carried out in the presence of a cobalt containing catalyst.

11. The process according to claim 9, wherein the oxidation is carried out in the presence of a cobalt containing catalyst and a manganese containing catalyst.

12. The process according to claim 8 wherein oxidation is carried out at a temperature from about 100° to about 200° C.

13. The process according to claim 8 wherein oxidation is carried out at a temperature from about 130° to about 180° C.

14. The process according to claim 8 wherein oxidation is carried out at a temperature from about 150° to about 170° C.

15. A process according to claim 1 wherein the oxidizing steps are carried out in the absence of an aliphatic monocarboxylic acid solvent.

16. A process according to claim 1 which comprises oxidizing the methyl p-toluate in a reaction vessel while feeding p-tolualdehyde- to said reaction vessel.

17. A process for producing terephthalic acid or an ester thereof which comprises the steps of
   (a) oxidizing at a first selected temperature a feedstock selected from the group consisting of p-tolualdehyde and p-tolualdehyde/p-xylene containing feedstocks with an oxygen-containing fluid to produce p-toluic acid; and
   (b) carrying out a step selected from the group consisting of
      (1) esterifying the product of step (a) with methanol to form methyl p-toluate and oxidizing at a second selected temperature the methyl p-toluate with an oxygen-containing fluid to form monomethyl terephthalate, and
      (2) oxidizing the product of step (a) with an oxygen-containing fluid to form terephthalic acid,
   wherein the oxidizing steps are carried out in the absence of any bromine compound.

18. A process according to claim 17 which comprises oxidizing the methyl p-toluate action vessel while feeding p-tolualdehyde- to said reaction vessel.

19. A process according to claim 1 wherein the oxidation of p-toluic acid and the oxidation of methyl p-toluate are carried out in the absence of a cobalt catalyst.

20. A process according to claim 19 wherein the oxidation of p-toluic acid and the oxidation of methyl p-toluate are carried out in the absence of a cobalt catalyst and in the absence of a manganese catalyst.

21. A process according to claim 1 wherein the feedstock is a p-tolualdehyde/p-xylene-containing feedstock which contains 5 to 90% p-tolualdehyde based on the total weight of p-tolualdehyde and p-xylene.

22. A process according to claim 15 wherein the oxidation of p-toluic acid and the oxidation of methyl p-toluate are carried out in the absence of a cobalt catalyst.

23. A process according to claim 22 wherein the oxidations are carried out at a temperature in the range of about 130° to about 180° C.

24. A process according to claim 23 wherein the oxidations are carried out at a temperature in the range of about 150° to about 170° C.

25. A process according to claim 15 wherein the oxidations are carried out at a temperature in the range of about 130° to about 180° C.

26. A process according to claim 8 wherein the oxidizing step is carried out in the absence of an aliphatic monocarboxylic acid solvent.

27. A process according to claim 26 wherein the oxidizing step is carried out at a temperature in the range of about 130° to about 180° C.

28. A process according to claim 16 wherein the methyl p-toluate is oxidized in a reaction vessel to which the p-tolualdehyde is added as a p-tolualdehyde/p-xylene mixture containing 5 to 95% p-tolualdehyde based on the total weight of p-tolualdehyde and p-xylene being added.

29. A process for the production of terephthalic acid and esters thereof, said process comprising at least the step of oxidizing a feed stock containing 5–90% p-tolualdehyde with an oxygen-containing fluid to terephthalic acid and esters thereof, wherein the formation of said esters is by the additional step of adding an alcohol at selected intervals during the oxidation process and includes the formation of methyl p-toluate and wherein said methyl p-toluate is oxidized to monomethyl terephthalate in a reaction vessel while p-tolualdehyde is fed to said vessel.

30. A process according to claim 29 which comprises oxidizing p-tolualdehyde to p-toluic acid and oxidizing p-toluic acid to terephthalic acid and wherein the oxidation of p-toluic acid and the oxidation of methyl p-toluate are carried out in the absence of a cobalt catalyst.

31. A process according to claim 30 wherein the oxidation of p-toluic acid and the oxidation of methyl p-toluate are carried out in the absence of a cobalt catalyst and in the absence of a manganese catalyst.

32. A process according to claim 31 wherein the oxidations are carried out at a temperature in the range of about 130° to about 180° C.

33. A process according to claim 32 wherein the oxidations are carried out at a temperature in the range of about 150° to about 170° C.

34. A process according to claim 30 wherein the oxidations are carried out at a temperature in the range of about 130° to about 180° C. and in the absence of a bromine compound.

35. A process according to claim 29 wherein the oxidations are carried out in the absence of a bromine compound.

36. A process according to claim 35 wherein the oxidations are carried out at a temperature in the range of about 130° to about 180° C.

37. A process according to claim 17 wherein the feedstock is a p-tolualdehyde/p-xylene-containing feedstock which contains 5 to 90% p-tolualdehyde based on the total weight of p-tolualdehyde and p-xylene.

38. A process according to claim 19 wherein the methyl p-toluate is oxidized in a reaction vessel to which the p-tolualdehyde is added as a p-tolualdehyde/p-xylene mixture containing 5 to 95% p-tolualdehyde based on the total weight of p-tolualdehyde and p-xylene being added.

39. A process for the production of dimethyl terephthalate which comprises the steps of:
   1. continuously introducing p-tolualdehyde, methyl p-toluate and an oxygen-containing fluid into an oxidizer which is maintained at conditions effective for the production of an oxidate reaction product comprising p-toluic acid and monomethyl terephthalate by oxidation of said p-tolualdehyde and said methyl p-toluate,
   2. continuously removing said oxidate reaction product from said oxidizer and continuously feeding it and methanol to an esterifier which is maintained under conditions effective to esterify said p-toluic acid to methyl p-toluate and to esterily said monomethyl terephthalate to dimethyl terephthalate,
   3. continuously removing esterified reaction product comprising methyl p-toluate and dimethyl terephthalate from said esterifier and separating the methyl p-toluate from the dimethyl terephthalate; and
   4. recycling the separated methyl p-toluate to the oxidizer.

40. A process according to claim 39 which comprises oxidizing p-tolualdehyde to p-toluic acid and oxidizing p-toluic acid to terephthalic acid and wherein the oxidation of toluic acid and the oxidation of methyl p-toluate are carried out in the absence of a cobalt catalyst.

41. A process according to claim 40 wherein the oxidation of p-toluic acid and the oxidation of methyl p-toluate are carried out in the absence of a cobalt catalyst and in the absence of a manganese catalyst.

42. A process according to claim 41, wherein the oxidations are carried out at a temperature in the range of about 130° to about 180° C.

43. A process according to claim 39 wherein step 1 is carried out in the absence of a bromine compound and in the absence of an aliphatic monocarboxylic acid solvent.

44. A process for producing monomethyl terephthalate which comprises the steps of
(a) oxidizing at a temperature in the range of about 100° to about 200° C. a feedstock selected from the group consisting of p-tolualdehyde- and p-tolualdehyde/p-xylene-containing feedstocks with an oxygen-containing fluid to produce p-toluic acid, and
(b) esterifying the product of step (a) with methanol to form methyl p-toluate and oxidizing at a temperature in the range of about 100° to about 200° C. the methyl p-toluate with an oxygen-containing fluid to form monomethyl terephthalate, wherein p-tolualdehyde is fed to a reaction vessel while the methyl p-toluate is being oxidized therein and is oxidized in the same reaction mixture in which the methyl p-toluate is oxidized.

45. A process according to claim 44 wherein the oxidations are carried out at a temperature in the range of about 130° to about 180° C. and in the absence of a bromine compound.

46. A process according to claim 45 wherein the oxidations are carried out in the absence of an aliphatic monocarboxylic acid solvent.

* * * * *